(12) United States Patent
Dugas et al.

(10) Patent No.: US 7,899,153 B2
(45) Date of Patent: Mar. 1, 2011

(54) AUTOMATED X-RAY FLUORESCENCE ANALYSIS

(75) Inventors: Michael E. Dugas, Londonderry, NH (US); Lee Grodzins, Lexington, MA (US); Stephen I. Shefsky, Brooklyn, NY (US)

(73) Assignee: Thermo Niton Analyzers LLC, Billerica, MA (US)

( * ) Notice: Subject to any disclaimer, the term of this patent is extended or adjusted under 35 U.S.C. 154(b) by 0 days.

(21) Appl. No.: 12/426,022

(22) Filed: Apr. 17, 2009

(65) Prior Publication Data
US 2009/0262889 A1 Oct. 22, 2009

Related U.S. Application Data

(60) Provisional application No. 61/045,925, filed on Apr. 17, 2008.

(51) Int. Cl.
*G01N 23/223* (2006.01)
(52) U.S. Cl. .............. 378/45; 378/57; 209/589
(58) Field of Classification Search .......... 378/45, 378/57; 209/589
See application file for complete search history.

(56) References Cited

U.S. PATENT DOCUMENTS

| | | | |
|---|---|---|---|
| 3,703,726 A | 11/1972 | Stevenson | |
| 6,519,315 B2 * | 2/2003 | Sommer et al. | 378/45 |
| 6,850,592 B2 * | 2/2005 | Schramm et al. | 378/45 |
| 7,170,970 B2 | 1/2007 | Tani et al. | |
| 7,366,282 B2 * | 4/2008 | Peschmann | 378/57 |
| 7,430,274 B2 | 9/2008 | Connors et al. | |
| 2006/0029182 A1 | 2/2006 | Tani et al. | |
| 2008/0205592 A1 | 8/2008 | Connors et al. | |

OTHER PUBLICATIONS

Yoshiyuki Kataoka, "Standardless X-Ray Fluorescence Spectrometry (Fundamental Parameter Method Using Sensitivity Library)," The Rigaku Journal, vol. 6 (1), 1989, pp. 33-40.

* cited by examiner

*Primary Examiner*—Edward J Glick
*Assistant Examiner*—Thomas R Artman
(74) *Attorney, Agent, or Firm*—Charles B. Katz

(57) ABSTRACT

A method for classifying a sample based upon a complete spectral analysis. The sample is illuminated with penetrating radiation and an initial complete spectral analysis is performed based on spectral resolution of resonant fluorescence lines emitted at the surface, or within the volume, of the sample. If the initial complete spectral analysis yields the composition of the sample to within acceptable limits, analysis values are output to the user. Otherwise, further analysis, informed by the results if the initial complete spectral analysis, is performed.

10 Claims, 3 Drawing Sheets

AUTOMATED X-RAY FLUORESCENCE ANALYSIS

The present application claims the priority of U.S. Provisional Patent Application Ser. No. 61/045,925, filed Apr. 17, 2008, which is incorporated herein by reference.

TECHNICAL FIELD

The present invention relates generally to preliminary automated characterization of the material composition of a sample to facilitate refinement of parameters for subsequent detailed analysis.

BACKGROUND ART

Definitions: As used in this description and in any accompanying claims, the following terms shall have the meanings indicated, unless the context otherwise requires:

The term "metal" is used herein to refer to a material composed of any element(s) belonging to the group of elements that, in their neutral ground state electronic configurations, readily lose one or more electrons to form positive ions. Without limitation, "metal" may refer to either a pure metal or alloy.

The term "predominantly non-metallic" denotes a material composition in which metals comprise only small fractions (<10%), including also trace fractions, by volume of the composition of a sample.

The term "mixed composition" denotes a collection of material, whether spatially homogeneous in composition or otherwise, wherein an appreciable fraction (>10%), by volume, of the material is metallic, and an appreciable fraction (>10%), by volume, of the material is non-metallic. The term "mixed composition", in its adjectival sense, is used herein interchangeably with the term "inhomogeneous."

The term "alloy" refers to a material that is predominantly metallic, and that is composed of more than a single element.

The term "complete spectral analysis" refers to a spectroscopic procedure wherein substantially all the x-ray fluorescence lines emitted by a sample within a specified range of the electromagnetic spectrum, and exceeding a specified signal strength, are employed to derive an estimate of the elemental composition of the sample. Other spectral features, other than lines, such as the shape of a scattering continuum, encompassing a portion (including the entirety) of the specified spectral range, may also be included, without limitation, in the complete spectral analysis. If only a small subset of lines within the specified spectral range is taken into account, then any resulting spectral analysis is not a "complete spectral analysis" within the meaning of the term as employed herein.

Current Practice: Field-portable x-ray fluorescence (XRF) instruments are used by inspectors throughout the world to determine the elemental distributions in a wide variety of sample matrices including soils, minerals, ceramics, metals, polymers, thin films, and paint on different substrates. The Thermo Scientific NITON® XL3, for example, employs various algorithms to properly analyze these different sample matrices. In general, a given instrument will be used in a specific instance for the analysis of a single class of samples, for example, sorting of alloys or the analysis of soil samples, or analysis of the paint in houses. In such cases, the most effective use of the analyzer is to operate in a single mode that the user selects from a menu on a touch screen or an associated computer.

There are, however, applications, in particular the measurement of toxic elements in consumer products, where any given product may contain several, or more, different materials. A costumed plastic doll is an example of a toy that may have cloth, leather-looking PVC parts, ceramic, and painted metal buttons. To obtain the correct analysis for each of these different materials requires the use of the correct settings of the XL3 and its corresponding analytic algorithms. Incorrect results will generally be reported if the wrong mode is chosen.

The most effective mode is often not obvious to the user, especially one not highly trained. For example, it may not be readily apparent to the user which of the available modes should be selected (which will typically be limited to a Metals Mode and a Plastics Mode) when inspecting items such as wood, fabric and foodstuffs. While the Plastics Mode is the most effective for analysis in such cases because all these materials are predominantly hydrocarbons, the user may be unlikely to know this fact.

XRF analyzers that determine the elemental concentration in materials make use of sophisticated analytic tools. To carry out the computational analysis as expeditiously as possible, it is normal practice to have the user cue the instrument as to the type of material dominating the object to be analyzed. In various Thermo Niton XRF analyzers, for example, cueing is performed by touching the appropriate icon, such as, for example, either "alloy" or "plastic," on a touch screen. Computer algorithms, starting with the generic information provided by the user, further refine the parameter space of analysis on the basis of the spectrum being collected. For example, the measurement of a metal, pre-designated by the user, will be sorted prior to full analysis as iron based, or copper based or zinc based depending on the strengths of the characteristic x-ray lines of iron, or copper or zinc. And the spectrum itself, by virtue of identified features, automatically allows the algorithm to select between polyvinyl chloride (PVC), for example, where chlorine is present, and other plastics that contain no major element heavier than oxygen.

U.S. Pat. No. 7,170,970 (to Tani et al.) teaches an automated algorithm to "[identify] or [judge]" whether the material is a "metal" or a "non-metal" on the basis of whether—or not—the sample emits fluorescent X-ray lines with a high spectrum intensity in response to short-time irradiation by x-rays. The pertinent teaching is found in col. 4, lines 1-10, of the patent of Tani et al. This method, while useful for certain prescribed applications, may not be well-suited to inspection of a broader range of materials of unknown composition.

Another patent, U.S. Pat. No. 7,430,274 (to Connors et al.), describes an inspection modality wherein an initial test is performed under a first setting of beam energy endpoint and beam filtration, and rates are determined for detected Compton scattering and fluorescence in a denumerated set of metal lines relative to the total detected count rate. Then, contingent upon a preliminary classification of the resulting detection, beam current is varied, and then one of a number of possible filters in inserted into the beam for subsequent measurements. This inspection modality will be referred to herein as a "contingent setting" inspection modality, since the set of beam and filter conditions under which final measurements are made is entirely contingent on the results of a first set of measurements.

SUMMARY OF THE INVENTION

In accordance with preferred embodiments of the present invention, a method is provided for classifying a composition of a sample of unknown composition. The method has steps of a. illuminating a portion of the sample with a first beam of penetrating radiation, the first beam characterized by a first pre-specified set of beam settings;

b. detecting x-ray emission emanating from the sample;

c. performing a complete spectral analysis of the x-ray emission; and d. categorizing the composition of the sample based on the complete spectral analysis at least with respect to metallic content.

In accordance with another embodiment of the present invention, a further method is provided that also serves to classify a composition of a sample of unknown composition. In the further method, the following steps are performed:

a. illuminating a portion of the sample with a first beam of penetrating radiation, the first beam characterized by a first pre-specified set of beam settings;

b. detecting x-ray emission emanating from the sample;

c. illuminating the portion of the sample with a second beam of penetrating radiation, the second beam characterized by a second pre-specified set of beam settings;

d. performing a complete spectral analysis of the x-ray emission; and e. categorizing the composition of the sample as one of predominantly non-metal and predominantly metal based on the complete spectral analysis.

In accordance with other embodiments of the invention, the step of performing a complete spectral analysis may include employing a Fundamental Parameter algorithm. The step of categorizing the composition of the sample may include determining whether the sample is one of predominantly non-metal and predominantly metal, and may be followed by a step of subsequently analyzing the sample contingent upon the categorization.

In alternate embodiments of the invention, the step of performing a complete spectral analysis of the emission may further include determining whether a concentration of chlorine exceeds a specified fractional weight composition. Based on a result of the step of categorizing the composition of the sample, a further step may include reanalyzing the emission in accordance with an alternate FP algorithm. This reanalyzing may also incorporate information provided by a user. Prior to reanalyzing, a further beam of penetrating radiation may be used to irradiate the sample, where the beam is characterized by a further set of beam settings that may include introduction of a filter in the beam, particularly a filter that may be made of iron, cobalt, or nickel.

BRIEF DESCRIPTION OF THE DRAWINGS

The invention will be more fully understood by referring to the following Detailed Description of Specific Embodiments in conjunction with the following Drawings.

DETAILED DESCRIPTION OF SPECIFIC EMBODIMENTS

Figure 1:
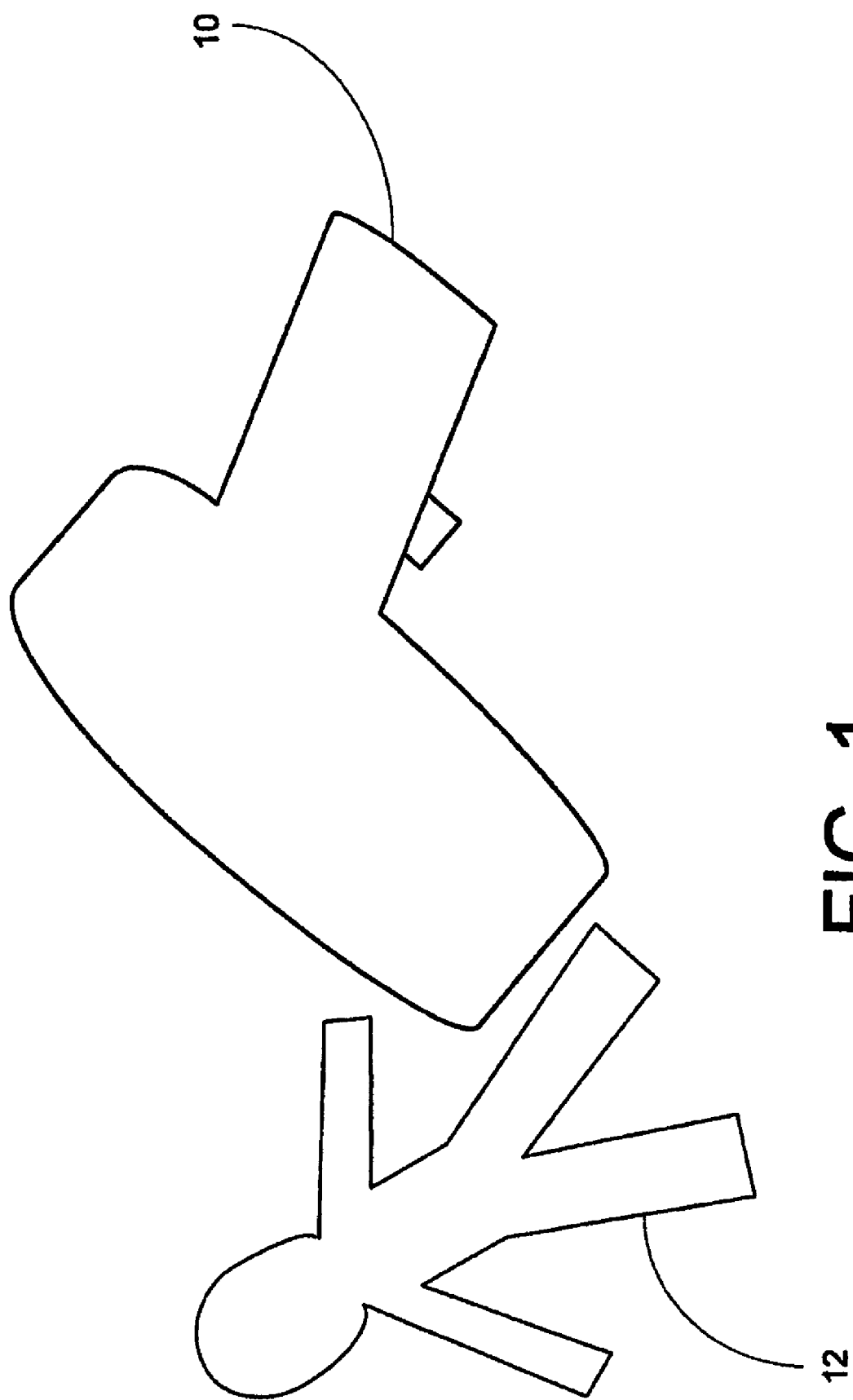
FIG. 1 depicts an XRF analyzer, of the sort to which the present invention may be applied, abutting a sample in preparation for analysis in accordance with the present invention.

The increasing capabilities of computers in small, low power packages have made practical the implementation of powerful algorithms in hand-held instruments. Embodiments of the present invention employ, without limitation to analysis using the Fundamental Parameter (FP) methods or any other specific algorithm, one or more iterative techniques employing successive manipulations of large matrix arrays whose parameters have been determined by factory calibrations of various materials that may be encountered; e.g. metals, plastics, soils, etc. The Fundamental Parameter method, with, or without, enhancements accounting for Compton scatter, is described, for example, by de Vries, et al., "Quantification of Infinitely Thick Specimens by XRF Analysis", in Van Grieken, et al., (eds.), *Handbook of X-Ray Spectrometry* ($2^{nd}$ Ed.), Chapter 5, (2005), the entirety of which volume is incorporated herein by reference. Further teaching is to be found in Sherman, *The Correlation Between Fluorescent X-Ray Intensity and Chemical Composition*, ASTM Special Publication No 157, (1953), pp. 27ff, which is also incorporated herein by reference.

In accordance with embodiments of the present invention, methods of analysis are described that do not require presorting into a binary (or other) set of material categories, and that, moreover, have the further important advantage of giving useful information about samples that are heterogeneous mixtures of metals and plastic. In accordance with the methods described, analysis of a wide variety of materials becomes possible by virtue of fully automatically adjusting the mode of analysis of data that has already been taken. The method is especially useful for analyzing consumer products by field-portable XRF instruments.

The power of the computation capabilities in the hand-held Thermo Niton XRF analyzers is sufficient to carry out, in less than 500 milliseconds, a complete analysis of a complex spectrum, involving up to 26 elements, with more than 10 iterations performed during that period. Simpler spectra require less time. In fact, the analytic time is so short that the several independent analyses may be performed in the course, say, of less than one second, with a result chosen on the basis of the best fit.

The recently introduced Thermo Scientific NITON® Model XL3 XRF analyzer, has the capabilities to rapidly analyze a multitude of materials, including PVC and non-PVC plastics, metals, non-plastic hydrocarbons, and heterogeneous compositions including more than one of the above, without any user input other than the initial selection of the automated mode. Composition analysis that does not require any user input as to the supposed type of material may be referred to herein as "adaptive analysis." A vital criterion for this mode to be effective in the marketplace is that it produce correct results rapidly. For example, an inspector of toys may wish to take more than 100 separate measurements per hour so that individual tests must be completed in fractions of a minute.

The differences in the spectra of metals and plastic are so marked that the analysis quickly converges to the correct parameter set, in cases where one set of parameters is to be employed for metals and another set for plastics. In other cases, differences between spectra obtained for a soil sample and spectra obtained for a mining ore sample, for example, may require substantially more iterations using different parameter sets, however the total analysis time may still be kept less than a second.

Figure 2:
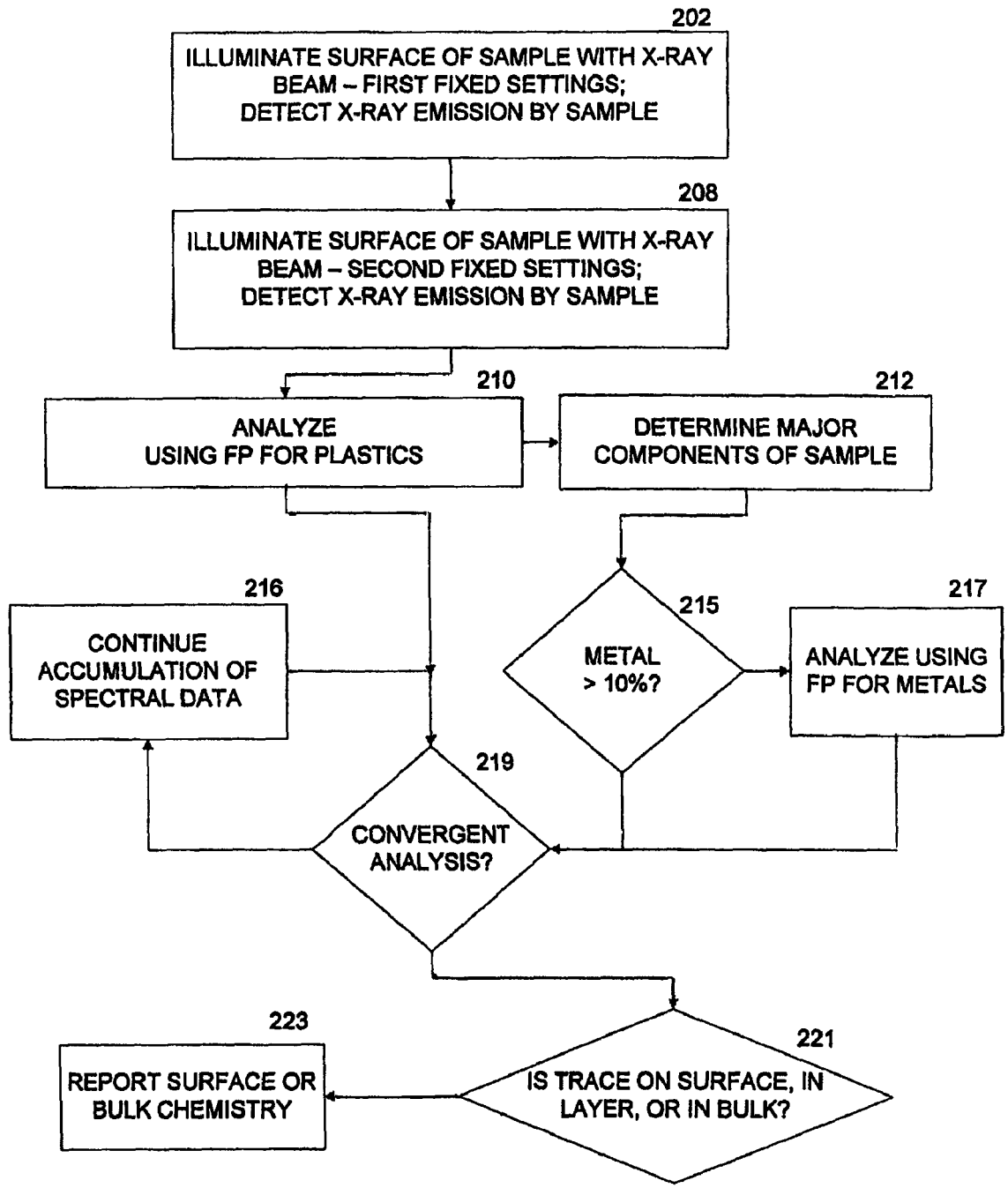
FIGS. 2 and 3 are flowcharts depicting method steps in the automated analysis of x-ray fluorescence in accordance with various embodiments of the present invention.

Steps of methods employed in accordance with preferred embodiments of the present invention are now described with reference to FIGS. 1 and 2. First, the sample 12, which may be of entirely unknown composition, is irradiated (in a step designated by numeral 202 in FIG. 2) with x-rays emanating from contained within XRF analyzer 10. Initial irradiation is typically performed using an x-ray tube (not shown) as a source, wherein the endpoint energy of the x-ray tube is 20 keV, and x-rays emitted by the source are filtered through a copper (Cu) filter. The use of an x-ray source, such as an x-ray tube, and the use of a window or elemental filter, such as a Cu filter or otherwise, are standard XRF techniques, described, for example, in U.S. Pat. No. 6,765,986, to Grodzins et al., which is incorporated herein by reference.

Radiation scattered by, or resonantly emitted (fluoresced) by, sample 12 is detected (202) and sorted in terms of energy within the analyzer. Again, the sorting by energy of fluoresced or scattered photons is standard XRF practice, and is described, for example, in U.S. Pat. No. 6,765,986. A signal, derived from the spectrally sorted x-ray emission, is then analyzed (210) in spectral analysis that is "complete," in the sense defined above. Any analysis program employed in analysis of XRF spectra may be used within the scope of the present invention. In particular, in accordance with a preferred embodiment of the present invention, an analysis program typically used to analyze a plastic sample is employed in a first complete spectral analysis. Such a standard analysis program is described by Van Grieken et al., supra. In performing the aforesaid analysis, no assumptions are made as to the composition of the sample. The initial spectral analysis, while "complete," may be referred to as a "precursory" or "preliminary" analysis, in that, if it is not definitive, it may be followed by a subsequent analysis under different conditions.

The preliminary complete spectral analysis (210), as described in the foregoing paragraph, may, more particularly, correspond to a Fundamental Parameter (FP) analysis, using initial parameters suitable for an analysis of plastics. The Fundamental Parameter-Plastics analysis, for example, allows for the sample to contain a dark matrix of hydrocarbon composition that does not give rise to measured fluorescent emission lines. Such an analysis is carried out using software loaded into a processor, typically contained within XRF analyzer 10. If the complete spectral analysis results in a fit of acceptable quality, i.e., within specified limits of certainty, then an analysis is displayed, or otherwise provided to the user.

Figure 3:
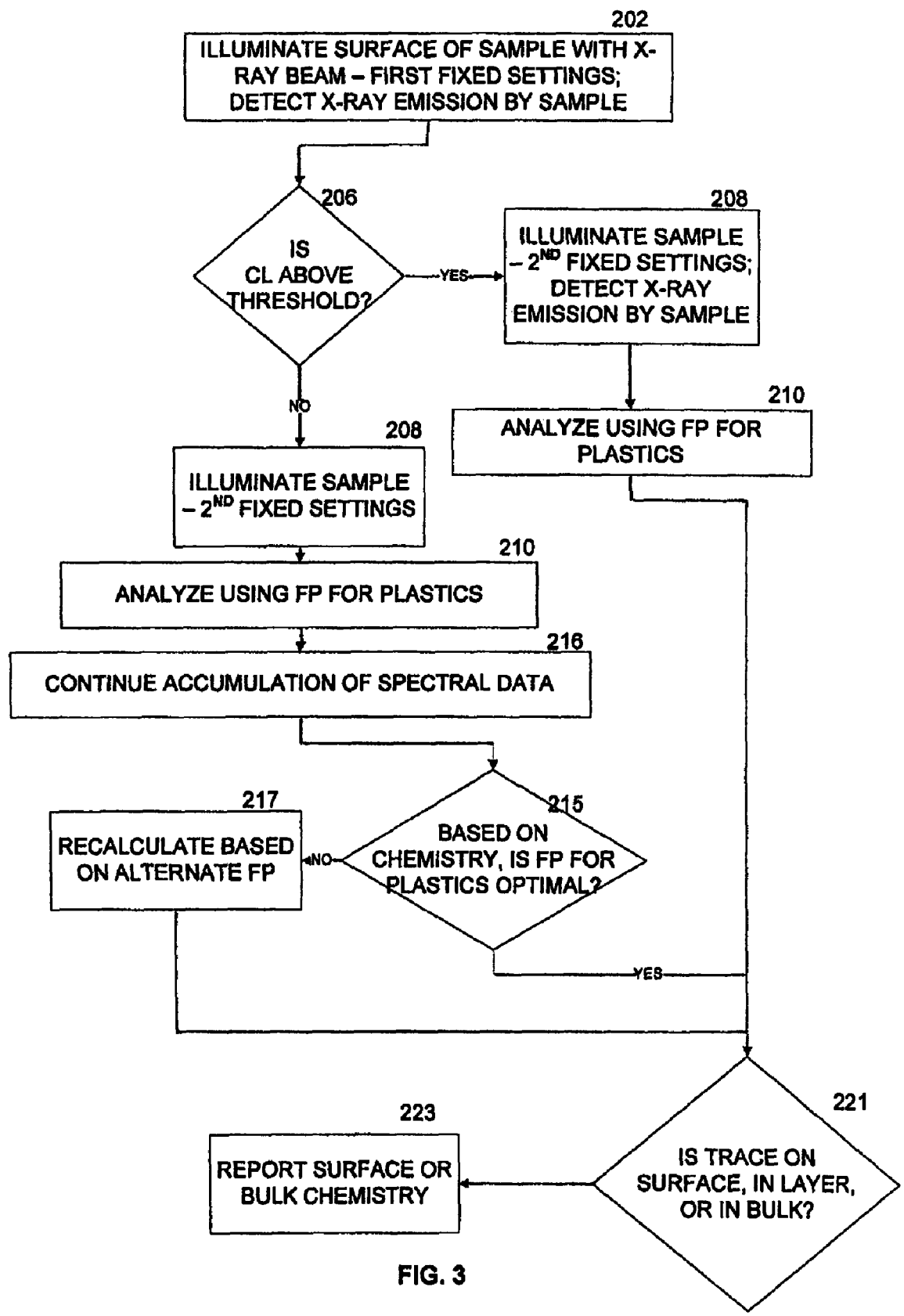

Based on the preliminary complete spectral analysis (210), it is determined, for example, whether chlorine (Cl) emission exceeds a specified compositional proportion, by mass, of the total sample composition. In the embodiment of the invention depicted in FIG. 3, the determination of chlorine content is made after irradiation by an initial set of beam conditions. The chlorine determination provides for subsequent analysis on the basis of an assumption that the inspected material contains PVC. In the embodiment depicted in FIG. 2, the conditions of irradiation may be changed to a second preconfigured set of conditions. Whereas, typically, the initial irradiation is performed at a tube voltage of 20 kV and a Cu filter, the second fixed set of irradiation conditions (208) may be a tube voltage of 50 kV and a molybdenum (Mo) filter. The first set of preconfigured irradiation parameters is particularly advantageous for the detection of fluorescence lines of lower-atomic-number metals, whereas the second set of preconfigured irradiation parameters is particularly advantageous for the detection of fluorescence lines of transition metals. However, it is to be understood that two fixed sets of settings may be used advantageously under certain conditions, whereas one or more sets of fixed settings may be used advantageously in other applications, all within the scope of the present invention. In any case, analysis of the XRF data obtained is performed (210) using a specified analysis that is not contingent, and that yields a complete spectral analysis, as defined above.

Complete spectral analysis, in step 210, provides for determining (212) major elemental components of sample 12. A trial solution is obtained for the chemistry of the sample. Based on outcomes of the complete spectral analysis, the same data obtained in step 202 (and 208, if present) may be analyzed using alternative FP analysis parameters. For example, if metal content exceeds a specified threshold (215), analysis may be repeated (217) using an FP calibrated for metals. The test may, alternatively, be set for one or more other thresholds based on one or more criteria. In another example, in the case of a heterogeneous sample, precursory elemental analysis may determine that there is no acceptable fit, in which case a re-analysis may be performed. The re-analysis may entail collection of further data, under different excitation conditions. Examples of such changed excitation conditions are provided below.

The data collected, and the analysis performed, during the course of the precursory analysis may serve to constrain, but not definitely determine, the elemental composition of the sample. I.e., the precursory analysis may determine that some elemental compositions are possible, and that some elements are present within determinable ranges of concentration, whereas the concentration, or even the presence, of other elements may remain uncertain.

For another example, if a precursor elemental analysis determines, on the basis of chlorine concentration, that the sample is predominantly PVC, then the sample may be reanalyzed accordingly.

Supplementing the automatic operation described above, the user may preset parameters, for example, the statistical uncertainty of specific elements such as the toxic elements whose maximum concentration is mandated by government regulations. In that case, data continue to be to accumulated (216), updating the chemistry and sample type reported to the user, repeating or changing the settings until the criteria are met or the system times out.

Typical criteria for closure for an adaptive analysis, in accordance with the present invention, may take different forms but are generally based on the convergence (219) of the fundamental parameter results. A standard criterion for FP analysis is for the analysis to terminate when the difference between the results, for all observed major and minor elements, obtained in the $n^{th}$ iteration differs by less than Y % from the results from the previous iteration. The number of iterations is seldom greater than four. The relative difference, Y %, for FP convergence is typically set at 0.001%, but may be as small as 0.0001%.

Methods practiced within the scope of the present invention may advantageously provide for the decision as to the optimal type of analysis to be performed is based solely on the results of a complete spectral analysis of detected spectral features and not a priori by a user. In particular, in a two component system, such a sample comprised of a single alloy and a single type of plastic, an acceptable fit for both may be obtained, in step 212, in the same analysis. The method is especially useful for analyzing consumer products by field-portable XRF instruments.

Once the chemical analysis of the sample has been performed, in accordance with the above description, other automated features may be advantageously incorporated, within the scope of the present invention. For example, a determination may be made, on the basis of detection of multiple lines of a single element, as to whether that species (typically lead (Pb) or another trace material), is disposed in a layer at, or near, the surface of the sample, or whether the trace material is distributed throughout the volume of the sample. A complete teaching in this regard, using multiple L-lines, where those are available in the detected fluorescence spectrum, is provided in U.S. patent application Ser. No. 12/205,678, to Grodzins et al., filed Sep. 5, 2008 and entitled "Measurement of Lead by X-Ray Fluorescence." During the analysis portion, multiple lines of a single element may be analyzed. Thus, for example, the lead L-alpha and L-beta peaks may be analyzed to determine (221) whether Pb is present on the surface or in the bulk of the material, or is buried beneath a layer of non-lead material. If Pb (or another target element) is determined to be on the surface of the sample or is in a buried layer, its concentration is calculated and reported (223) in units of $\mu g/cm^2$, or comparable units. If the Pb is in the bulk, lead concentration, as with all other elements, is reported in mg/kg or in percent.

The integrated results from all modes determine the composition of the elements, together with their statistical uncertainties, the identification of the material, and, where applicable, other characteristics such as the thicknesses of the materials.

Another particular exemplary embodiment of the methods of the present invention is now described. In this description, the use of a Thermo Scientific Niton® XL3 is assumed. The parameters of the x-ray tube can be automatically changed in 200 ms to produce beams of electrons that range from 5 keV to 50 keV with currents that range up to 220 µA. The beam profile of the generated x-ray beam can be changed in approximately 100 ms by inserting in the beam path one of the filters on a six-position filter wheel. It will be appreciated, that these performance characteristics are illustrative. Different x-ray tubes with different modes for manipulating the x-ray beams may be used.

In general, every sample is analyzed by as many settings and algorithms as is necessary for the analyzer to reach closure on results. Tests most typically begin with data taken at two fixed settings (202, 208). The analysis of those data determines the next settings so that each successive new setting of parameters or algorithms is based on the preceding accumulated results.

In the first set of fixed settings (202), in accordance with the exemplary embodiment, the voltage on the x-ray tube and the filter are set to rapidly examine the spectra from lighter elements. The duration of illumination is in the range of 2 to 3 seconds. In a more particular example, the tube voltage is set at 20 keV and a copper filter is used to give a first analysis of the concentration of lighter elements. The x-ray tube current is automatically adjusted so that the count rate in the detector is optimized to produce the maximum counts in the shortest time. The optimization is based on a "dead time" of 50%; that is, the electron beam current is adjusted (in tens of milliseconds) so that approximately 50% of the elapsed time is spent accumulating data. In the XL3, the "dead time" criterion results in a throughput count rate of at least 10,000 counts per second so that the system accumulates at least 20,000 counts in about 2 seconds, which is sufficient for a preliminary analysis.

In the second set of fixed settings (208), in accordance with the exemplary embodiment, a higher tube voltage is provided, along with a filter of higher atomic number than the filter of the first set of fixed setting. Possible filter elements include, for example, iron, cobalt, and nickel. The duration of the second illumination is determined by closure of the chemical analysis and is not limited a priori. As a more specific example, the high voltage may be changed to 50 kV, with the current, again, set to produce an optimum high counting rate. The filter is changed to molybdenum, which produces an x-ray spectrum with a strong fluorescing x-ray of 17.5 keV.

The data obtained at the first Setting is analyzed in about one second to give a measure of the elemental composition of the spectrum. The chemistry of the sample thus obtained gives a preference to the Fundamental Parameter (FP) method that will be first used to analyze the data being obtained at Setting 2. For example, if Setting 1 has determined that the sample is most likely PVC, then only the FP mode most suitable for plastics may be the first used.

The accumulated data, together with the intensities of the Compton and coherent scatter peaks are continuously used to determine the best values for the concentration of the elements and to identify the type of material.

In some applications, only two settings are required to obtain the concentration of the elements to sufficient accuracy to give assurance that the chosen analytic mode is correct. In that case the analysis will stop and the results will be presented. Typical test durations are 10 seconds.

In various situations, the analysis will continue. Examples are provided by the following scenarios:

Example 1

The spectrum obtained in Step 2 may show evidence of significant concentrations of elements such as molybdenum or its neighbors. These concentrations cannot be accurately measured with a molybdenum filter.

Example 2

The results from Steps 1 and 2, may show a concentration of calcium that makes plausible the presence of an associated element such as strontium. In that case, a more effective analysis is provided by another (non-molybdenum) filter.

In both of the foregoing examples, a silver (Ag) filter is inserted in the beam path, and the beam current is adjusted. The resultant irradiation conditions constitute Setting 3.

In a further example, if statistical uncertainties remain large and do not decrease with time according to statistical rules, the system may determine (in step 212) that the first FP method was not the most suitable for the sample, and, in continuation of Step 2, it re-calculates the data (217) utilizing a second available FP model. Alternatively, the accumulated data may continuously be analyzed with more than one FP method with the final result best on the best fit to all the data.

In yet a further example, the Compton and Rayleigh scattering strengths may indicate the presence of very light elements. In this case, in accordance with the invention, the system will change the parameters to obtain a measure of the aluminum, silicon and other light elements in the sample.

Supplementing the automatic operation described above, the user may preset parameters, for example, the statistical uncertainty of specific elements such as the toxic elements whose maximum concentration is mandated by government regulations. In that case, data continue to be to accumulated, updating the chemistry and sample type reported to the user, repeating or changing the settings until the criteria are met or the system times out.

Typical criteria for closure for an adaptive analysis mode may take different forms, in accordance with various embodiments of the present invention, but are generally based on the convergence of the fundamental parameter results. A standard criterion for FP analysis is for the analysis to terminate when the difference between the results, for all observed major and minor elements, obtained in the $n^{th}$ iteration differs by less than Y % from the results from the previous iteration. The number of iterations is seldom greater than four. The relative difference, Y %, for FP convergence is typically set at 0.001%, but may be as small as 0.0001%.

An important feature of this approach is that the computer retains the history of all the spectra obtained in a given test.

No data are lost or thrown away, even when the data are analyzed by different methods in order to obtain the optimum fit.

While the invention is described through the above-described exemplary embodiments, it will be understood by those of ordinary skill in the art that modifications to, and variations of, the illustrated embodiments may be made without departing from the inventive concepts disclosed herein. Moreover, disclosed aspects, or portions of these aspects, may be combined in ways not listed above. Accordingly, the invention should not be viewed as being limited to the exemplary embodiments.

What is claimed is:

1. A method for classifying a composition of a sample of unknown composition, the method comprising:

illuminating a portion of the sample with a first beam of penetrating radiation, the first beam characterized by a first pre-specified set of beam settings;

detecting x-ray emission emanating from the sample;

illuminating the portion of the sample with a second beam of penetrating radiation, the second beam characterized by a second pre-specified set of beam settings;

performing a complete spectral analysis of the x-ray emission; and categorizing the composition of the sample as one of predominantly non-metal and predominantly metal based on the complete spectral analysis.

2. A method in accordance with claim 1, wherein the step of performing a complete spectral analysis includes employing a Fundamental Parameter algorithm.

3. A method in accordance with claim 1, wherein the step of categorizing the composition of the sample includes determining whether the sample is one of predominantly non-metal and predominantly metal.

4. A method in accordance with claim 1, wherein the step of categorizing the composition of the sample is followed by a step of subsequently analyzing the sample contingent upon the categorization.

5. A method in accordance with claim 1, wherein the step of performing a complete spectral analysis of the emission further comprises determining whether a concentration of chlorine exceeds a specified fractional weight composition.

6. A method in accordance with claim 1, wherein, based on a result of the step of categorizing the composition of the sample, the method comprises a further step of reanalyzing the emission using a set of analysis parameters corresponding to the sample composition category.

7. A method in accordance with claim 6, wherein the step of reanalyzing emission is based, additionally, upon information provided by a user.

8. A method in accordance with claim 6, further comprising a step, prior to reanalyzing, of illuminating a portion of the sample with a further beam of penetrating radiation, the further beam characterized by a further set of beam settings.

9. A method in accordance with claim 8, wherein the step of illuminating a portion of the sample with a further beam of penetrating radiation includes inserting a filter in the further beam.

10. A method in accordance with claim 9, wherein the filter includes at least one of iron, cobalt, and nickel.

* * * * *